United States Patent [19]
Kawashima et al.

[11] Patent Number: 5,486,544
[45] Date of Patent: Jan. 23, 1996

[54] POLYMERIZABLE COMPOSITION

[75] Inventors: Mitsunobu Kawashima; Ikuo Omura, both of Kurashiki, Japan

[73] Assignee: Kuraray Co., Ltd., Kurashiki, Japan

[21] Appl. No.: 304,434

[22] Filed: Sep. 12, 1994

Related U.S. Application Data

[63] Continuation of Ser. No. 895,170, Jun. 8, 1992, abandoned, which is a continuation of Ser. No. 550,508, Jul. 10, 1990, abandoned.

[30] Foreign Application Priority Data

Jul. 12, 1989 [JP] Japan ..................... 1-181382

[51] Int. Cl.$^6$ .................................... C08F 2/46
[52] U.S. Cl. ................. 522/17; 522/15; 526/172; 526/173; 526/217; 526/222; 526/225; 206/813
[58] Field of Search ................. 522/15, 17; 526/172, 526/173, 217, 222, 225; 206/813

[56] References Cited

U.S. PATENT DOCUMENTS 4,816,495  3/1989  Blackwell et al. .................... 522/17

OTHER PUBLICATIONS

*Organic Chemistry;* Morrison and Boyd; Allyn and Bacon, Inc., Boston, 1975, pp. 35–36.
"The Chemistry of Sulphinic Acids, Esters and their Derivatives", pp. 639, 648–651, 662–663 (1990).
"Chem. Rev.", vol. 48, pp. 69–124 (1951).
"Journal of Polymer Science", vol. XL, pp. 179–201 (1959).

*Primary Examiner*—Mark A. Chapman
*Attorney, Agent, or Firm*—Oblon, Spivak, McClelland, Maier & Neustadt

[57] ABSTRACT

A polymerizable composition comprising:
(a) a monomer; and
(b) a sulfinate represented by the formula (I):

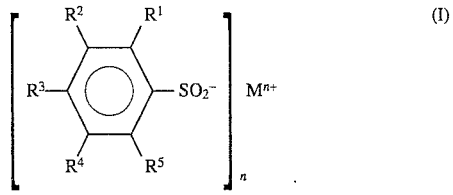

wherein $R^1$ and $R^5$ each represents a substituent having 2 to 6 carbon atoms, $R^2$, $R^3$ and $R^4$ each represents an atom or substituent inert to the monomer (a), $M^{n+}$ represents a n-valent cation, and n represents an integer of 1 to 4.

20 Claims, No Drawings

POLYMERIZABLE COMPOSITION

This application is a continuation of application Ser. No. 07/895,170, filed on Jun. 8, 1992, now abandoned, which is a continuation of application Ser. No. 07/550,508, filed on Jul. 10, 1990, now abandoned.

BACKGROUND OF THE INVENTION

1. Field of the Invention

The present invention relates to polymerizable compositions, and more particularly to polymerizable compositions with excellent storage stability containing an aromatic sulfinate as a polymerization initiator.

2. Description of the Background

There is known as a means for polymerizing radical-polymerizable monomers the use of a sulfinic acid or a salt thereof, such as sulfinic acids, sulfinic acid or a salt-oxidizer system thereof, and sulfinic acid or a salt-amine-peroxide system thereof, as a component of a polymerization initiator. For example Japanese Patent Application Laid-open No. 30193/1978 discloses a process entailing the use of a sulfinate-amine-peroxide system as a polymerization initiator for radical-polymerizable monomers. Further Japanese Patent Application Laid-open No. 75907/1982 discloses that this sulfinate-amine-peroxide system is particularly useful for the polymerization of dental adhesives comprising an acidic monomer.

However, since aromatic sulfinates which have hitherto been used, e.g. benzenesulfinate and toluenesulfinate, gradually react with the double bond of the monomers such as (meth)acrylate, (meth)acrylamide or (meth)acrylamide derivative, compositions comprising the sulfinate dissolved or suspended in the monomer will lose the polymerization activity in a few weeks when stored at room temperature.

Thus, the two components must be stored in separate packages so that they wily not be in contact with each other. However, this is very disadvantageous compared to other systems which can be packed and stored together with both monomer and initiator.

Therefore, a need continues to exist for a composition containing a polymerizable monomer and a sulfinate, which composition has an extended storage stability.

SUMMARY OF THE INVENTION

Accordingly, it is an object of the present invention to provide a composition containing a polymerizable monomer and a sulfinate, which composition has an extended storage stability.

The above object and others which will become more apparent in view of the following are provided by a polymerizable composition, containing:

a) a monomer; and b) a sulfinate having the formula (I):

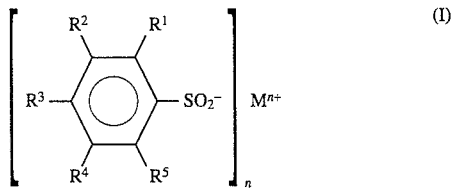

wherein $R^1$ and $R^5$ each represents a substituent having 2 to 6 carbon atoms; $R^2$, $R^3$ and $R^4$ each represents an atom or substituent inert to the monomer; $M^{n+}$ represents a n-valent cation, and n represents an integer of 1 to 4.

In accordance with the present invention, it has now been discovered that by introducing bulky substituents into positions 2 and 6 of aromatic sulfinates, it is possible to dramatically suppress the addition of these sulfinates to the double bond of (meth)acrylates, (meth)acrylamides or derivatives thereof.

Thus, the present invention provides a composition comprising:

(a) a monomer; and (b) a sulfinate represented by the formula

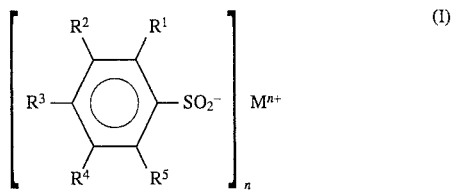

wherein $R^1$ and $R^5$ each represents a substituent having 2 to 6 carbon atoms; $R^2$, $R^3$ and $R^4$ each represents an atom or substituent inert to the monomer; $M^{n+}$ represents a n-valent cation, and n represents an integer of 1 to 4.

The present invention is characterized by the use of aromatic sulfinates represented by the formula (I) having bulky substituents in positions 2 and 6.

In the above-mentioned formula (I), $R^1$ and $R^5$ each is a substituent located in the ortho-position to the sulfinate group of the aromatic sulfinate, each having sufficient bulkiness for exerting steric hindrance to addition of the sulfinate group to the carbon-carbon double bond of a monomer. It is important that both $R^1$ and $R^5$ be bulky groups. If only one of the two groups is bulky, sufficient steric hindrance to the addition of the sulfinate group to the double bond will not be exerted to achieve the object of the present invention. With respect to the bulkiness of the groups, although a carbon atom number of 1, i.e. methyl group, may suppress the addition reaction, as a practical matter the effect of the present invention is attained with a carbon atom number of at least 2, particularly at least 3. While the addition is suppressed to a larger extent with an increasing number of carbon atoms, the effect of the suppression will become smaller once the substituent has a bulkiness of a certain degree. In view of this and the commercial availability of raw materials, the number of carbon atoms used is up to 6 for practical purposes. $R^1$ and $R^5$ should, naturally, be inert to the double bond of the monomer. Thus, $R^1$ and $R^5$ each is a hydrocarbon group which has 2 to 6 carbon atoms and may be substituted with one or more halogen atoms. Examples of $R^1$ and $R^5$ are ethyl, 2-chloroethyl, 2-bromo-2-chloroethyl, propyl, isopropyl, perfluoropropyl, allyl, butyl, isobutyl, sec-butyl, tert-butyl, pentyl, isopentyl, neopentyl, tert-pentyl, cyclohexyl, phenyl, 4-bromophenyl and the like.

$R^2$, $R^3$ and $R^4$ may be any atom and/or group as long as they are inert to the double bond of monomers. Examples thereof are hydrogen, fluoro, chloro, bromo, iodo, methyl, ethyl, 2-chloroethyl, 2-bromo-2-chloroethyl, propyl, isopropyl, perfluoropropyl, allyl, butyl, isobutyl, sec-butyl, tert-butyl, pentyl, isopentyl, neopentyl, tert-pentyl, cyclohexyl, phenyl and 4-bromophenyl.

$M^{n+}$ is a cation with mono-valency to tetra-valency that can, as a counter ion for a sulfinic acid anion, form the sulfinate. Examples of $M^{n+}$ are alkali metal ions, such as $Li^+$, $Na^+$, $K^+$, $Rb^+$ and $Cs^+$, alkali earth metal ions, such as $Be^{2+}$, $Mg^{2+}$, $Ca^{2+}$, $Sr^{2+}$ and $Ba^2$, transition metal ions, such as $Cr^{2+}$, $Cr^{3+}$, $Mn^{2+}$, $Fe^{2+}$, $Fe^{3+}$, $Co^{2+}$, $CO^{3+}$, $Ni^{2+}$, $Cu^{2+}$, $Zn^{2+}$ $Rh^{3+}$, $Pd^{2+}$, $Ag^+$, $Cd^{2+}$, $Ir^{3+}$, $Ir^{4+}$ and $Hg^{2+}$, and ammonium ions, such as $NH_4^+$, $(CH_3CH_2)_3NH^+$,

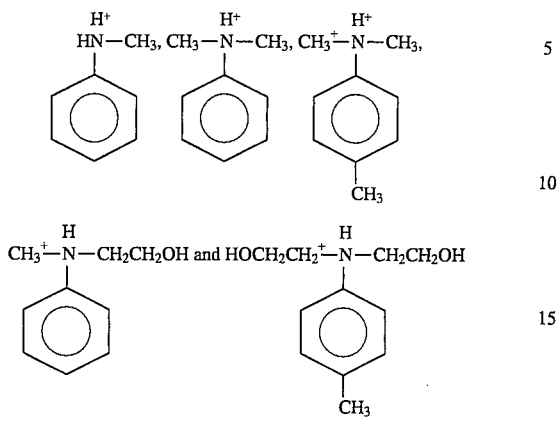

Preferred counter ions among these ions are $Li^+$, $Na^+$, $K^+$, $Mg^{2+}$ and $Ca^{2+}$, since sulfinates therefrom are excellent in stability when stored in monomers and have good solubility in the monomers.

Examples of the sulfinate represented by the formula (I) are as follows:

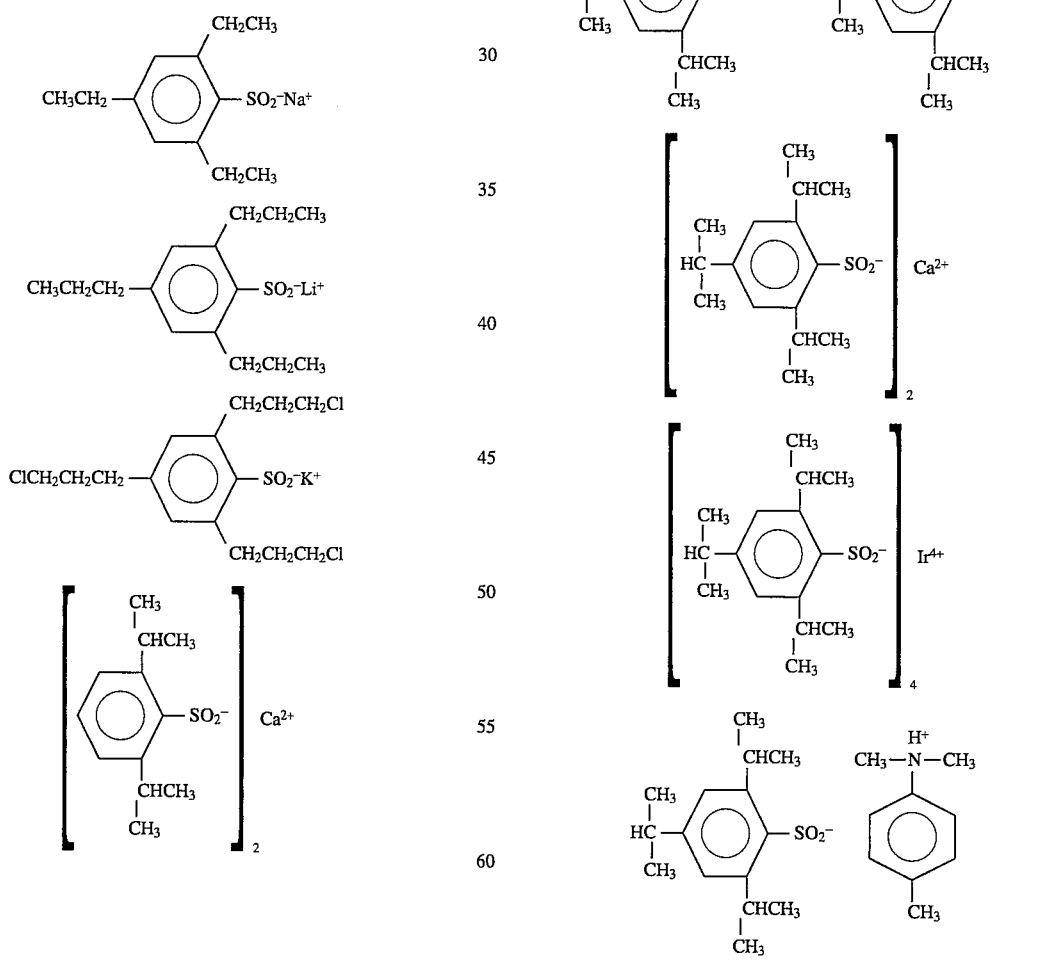

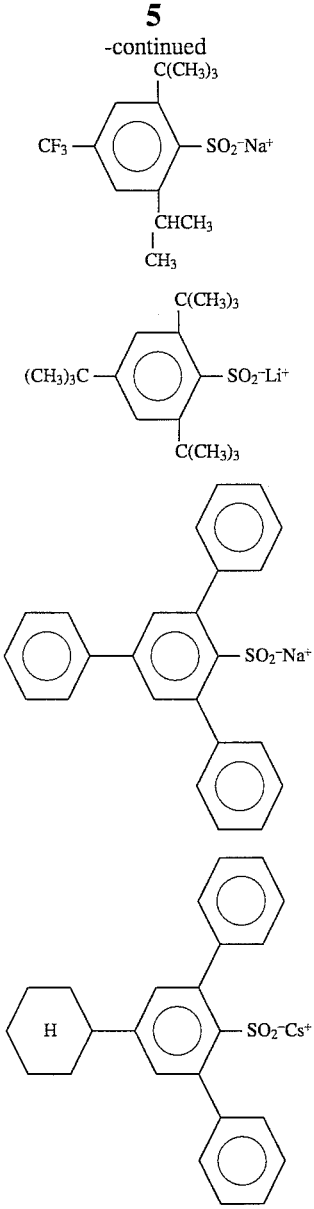

An advantageous use of the present invention may be found, perhaps most, with monomers having a carbon-carbon double bond directly linked to an electron attractive group such as —F, —Cl, —Br, —I, —CN, —NO$_2$, —NO, —CO—, —CS—, —COO—, —COS—, —CSO—, —CSS—, —CONH$_2$, —CONH— or —CON—. Where monomers without the above electron attractive groups, such as styrene, butadiene and allyl alcohol are used, sufficient storage stability is secured with conventional benzenesulfinates and toluenesulfinates. With monomers having the above electron attractive groups, these conventional sulfinates, however, do not exhibit practical storage stability because of the occurrence of an addition reaction.

Among monomers having a carbon-carbon double bond directly linked to an electron attractive group, particularly suited for the purpose of the present invention are (meth)acrylates, α-haloacrylates, (meth)acrylamides and derivatives thereof, represented by the formula:

$$\begin{array}{c} R^6 \\ | \\ H_2C=C-COXR^7(R^8)_m \end{array}$$

wherein $R^6$ represents a hydrogen atom, methyl group or halogen atom, $R^7$ and $R^8$ each represents a hydrogen atom or an organic group which may contain $$\begin{array}{c} R^6 \\ | \\ H_2C=C-COX-, \end{array}$$

X represents an oxygen atom or nitrogen atom and m represents 0 where X is an oxygen atom and represents 1 where X is a nitrogen atom.

Examples of the monomer represented by the above general formula are as follows. In the present invention the expression "(meth)acryl" means both methacryl and acryl.

(a) Monofunctional (meth)acrylates

Methyl (meth)acrylate, ethyl (meth)acrylate, iso-butyl (meth)acrylate, n-hexyl (meth)acrylate, benzyl (meth)acrylate, decyl (meth)acrylate, lauryl (meth)acrylate, 2-hydroxyethyl (meth) acrylate, 2-(N,N-dimethylamino)ethyl (meth) acrylate, 2,3-dibromopropyl (meth)acrylate, oxiranylmethyl (meth) acrylate, and 3-methacryloyloxypropyltrimethoxysilane, for example.

(b) Bifunctional (meth)acrylates

Ethylene glycol di(meth)acrylate, diethylene glycol di(meth)acrylate, triethylene glycol di(meth)acrylate, propylene glycol di(meth)acrylate, dipropylene glycol di(meth)acrylate, neopentyl glycol di(meth)acrylate, 1,6-hexanediol di(meth)acrylate, 1,10-decanediol di(meth)acrylate, bisphenol-A-di(meth)acrylate, 2,2-bis((meth)acryloyloxyethoxyphenyl)propane, 2,2-bis((meth)acryloyloxypolyethoxyphenyl)propane, 2,2-bis[4-(3-(meth)acryloyloxy-2-hydroxypropoxy)phenyl] -propane, and 1,2-bis(3-(meth)acryloyloxy-2-hydroxypropoxy)ethane, for example.

(c) Tri- or more functional (meth)acrylates

Trimethylolpropane tri(meth)acrylate, trimethylolethane tri(meth)acrylate, tetramethylolmethane tri(meth) acrylate, and pentaerythritol tetra(meth)acrylate, for example.

(d) α-Haloacrylates

α-Fluoromethyl acrylate, α-chloromethyl acrylate, α-fluoroethyl acrylate, α-chlorobutyl acrylate, and α-fluoro-2,2,2-trifluoroethyl acrylate, for example.

(e) (Meth) acrylamide derivatives (Meth) acrylamide, N-methyl(meth)acrylamide, N-isopropyl(meth) acrylamide, N-n-octyl(meth)acrylamide, N-benzyl (meth)acrylamide, N-(2-hydroxyethyl) (meth)acrylamide, N-(2-dimethylaminoethyl) (meth)acrylamide, N,N-dimethyl(math)acrylamide, N,N-dicyclohexyl(meth)acrylamide, N-methyl-N-phenyl(meth)acrylamide, N,N'-methylenebis(meth)acrylamide, and 1,6-bis-(meth)acrylamidehexane, for example.

These copolymerizable monomers may be used singly or in combination.

The composition of the present invention is obtained by dissolving or suspending the compound represented by formula (I) in the above monomer. The sulfinate represented by formula (I) is used in an amount of 0.01 to 10% by weight based on the weight of the composition, preferably in an amount of 0.03 to 5% by weight on the same basis.

Since the composition of the present invention is by itself extremely slow in initiating polymerization at room temperature, polymerization is effected by adding an oxidizer or by adding a photoinitiator, followed by photoradiation.

As the oxidizer used in the invention, organic peroxides capable of initiating polymerization by redox reaction with sulfinates are employed, and diacyl peroxides are preferred. Examples of the diacyl peroxides include, among others, benzoyl peroxide, m-toluoyl peroxide, 2,4-dichloro-benzoyl peroxide, octanoyl peroxide, lauroyl peroxide and succinoyl peroxide, among which particularly preferred are aromatic peroxides such as benzoyl peroxide and m-toluoyl peroxide. The oxidizer is stored in a package avoiding contact with the sulfinate represented by formula (I), and is, in polymerizing the composition of the present invention, added to the sulfinate in an amount of 0.01 to 500 parts by weight based on 1 part by weight of the sulfinate. An amine may further be added to the sulfinate and oxidizer system to form a ternary initiator, whereby polymerization is much more accelerated. In this case, while the amine can be stored while being in contact with the sulfinate with no problem, the amine must not contact the oxidizer for inhibition of premature polymerization. In packaging the sulfinate and the oxidizer separately, the amine is therefore packed together with the sulfinate. Aromatic secondary or tertiary amines are preferred for this purpose, and their examples are N,N-dimethylaniline, N,N-dimethyl-p-toluidine, ethyl m-N,N-dimethylaminobenzoate, ethyl p-N,N-dimethylaminobenzoate, N,N-diethanolaniline, N,N-diethanol-p-toluidine, N,N-diethanol-m-chloroaniline, N,N-bis(3-hydroxypropyl)aniline, N,N-bis(3-hydroxypropyl)-p-toluidine, N,N-bis(2,3-dihydroxypropyl)aniline, N,N-bis(2,3-dihydroxypropyl)-p-toluidine, ethyl m-N,N-bis(2,3-dihydroxypropyl)aminobenzoate, N-methylaniline, and N-methyl-p-toluidine. The amine is added in an amount of 0.01 to 500 parts by weight based on 1 part by weight of the compound represented by formula (I).

Suitable photoinitiators are photosensitive dyes and α-diketones, and their examples are Methylene blue, Eosin YS, diacetyl, 2,3-pentanedione, 2,3-hexanedione, 3,4-hexanedione, camphorquinone, bicyclo-[2.2.1]heptane-2,3-dione, acenaphthenequinone, 9,10-phenanthraquinone, and 9,10-anthraquinone, for example. The photoinitiator is added in an amount of 0.01 to 500 parts by weight based on 1 part by weight of the compound of formula (I).

The composition of the present invention can comprise both the oxidizer and the photoinitiator and be subjected to both redox and photopolymerization.

On the other hand, where the composition of the present invention is used as a primer, on which another polymerizable composition is applied, polymerization is effected by an initiator which has been contained in the other polymerizable composition and has migrated to the composition of the present invention, even when the composition of the present invention has not originally contained an oxidizer or photoinitiator.

The composition of the present invention may further comprise, as required, additives other than the above components, such as inorganic filler, polymer, organic solvent, polymerization inhibitor, antioxidant, ultraviolet absorber, pigment and dye, for example. When a polymer is added, it can be added either as an insoluble filler or as a thickener, which is soluble in the composition.

As stated heretofore, introduction of bulky groups into positions 2 and 6 of a benzenesulfinate can suppress the rate of addition reaction of the sulfinate to the double bond of the monomer below 1/10 that in the case conventional benzenesulfinates or toluenesulfinates are used. Then, while compositions containing conventional sulfinates can be stored at room temperature stably only for a few weeks, the compositions of the present invention can be stored at room temperature stably for at least one year and thus have significant practical advantage.

The polymerizable composition of the present invention can polymerize rapidly by addition of an oxidizer or by addition of a photoinitiator, followed by photoradiation. The present composition can be used as adhesives for various industrial uses and as moldable resins. One of the suitable uses of the composition is in denistry where it is used as a dental adhesive.

The present invention will now be further described by reference to certain Examples which are provided solely for purposes of illustration and which are not intended to be limitative.

EXAMPLES

Examples 1 through 7 and Comparative Examples 1 through 8

As sulfinates, sodium 2,4,6-triethylbenzenesulfinate, sodium 2,4,6-triisopropylbenzenesulfinate, lithium 2,4,6-triisopropylbenzenesulfinate, calcium 2,6-diisopropylbenzenesulfinate, lithium 2,4,6-tri-tert-butylbenzenesulfinate and sodium 2,4,6-triphenylbenzenesulfinate were used, and, as the polymerizable monomers, 2-hydroxyethyl methacrylate and a mixture of 2,2-bis [4-(3-methacryloyloxy-2-hydroxypropoxy)phenyl]propane, triethylene glycol dimethacrylate and 1,2-bis (3-methacryloyloxy-2hydroxypropoxy)ethane were used, to prepare compositions of Examples 1 through 7 as shown in Table 1. These compositions were each placed in a glass ampule tube, which was then sealed by fusion, and the tubes with their contents were stored at 37° C. for 14 days. The amounts of the sulfinates before and after the storage were determined by high-performance liquid chromatography, and the ratios of remaining sulfinates after the storage at 37° C. for 14 days were calculated. The results are shown in Table 1. The above procedures were repeated except for using, instead of the sulfinates used in Examples 1 through 7, sodium benzenesulfinate, sodium p-toluenesulfinate, sodium p-ethylbenzenesulfinate, sodium pisopropylbenzenesulfinate, calcium p-isopropylbenzenesulfinate, calcium o-isopropylbenzenesulfinate and sodium 2,4,6-trimethylbenzenesulfinate, to prepare compositions of Comparative Examples 1 through 8.

Regardless of the absence or presence, or the type, of substituent in position 4, the introduction of substituents having at least 2 carbon atoms into positions 2 and 6 significantly increased the retention of sulfinate. Where a substituent having at least 2 carbon atoms was introduced into only position 2 and where methyl groups were introduced into positions 2 and 6, there were observed some improvement in retention, which fell, however, far short of the retention achieved in the case where substituents having at least 2 carbon atoms were introduced in both positions 2 and 6.

TABLE 1

| | Components of Composition | | | | Retention of sulfinate (%) |
|---|---|---|---|---|---|
| | Monomer; | parts by weight | Sulfinate; | parts by weight | |
| Example 1 | 2-hydroxyethyl methacrylate | 100 | sodium 2,4,6-triethylbenzenesulfinate | 1 | 82 |
| Example 2 | 2-hydroxyethyl methacrylate | 100 | sodium 2,4,6-triisopropylbenzenesulfinate | 1 | 90 |
| Example 3 | 2-hydroxyethyl methacrylate | 100 | lithium 2,4,6-triisopropylbenzenesulfinate | 1 | 92 |
| Example 4 | 2-hydroxyethyl methacrylate | 100 | lithium 2,4,6-tri-tert-butylbenzenesulfinate | 1 | 95 |
| Example 5 | 2-hydroxyethyl methacrylate | 100 | sodium 2,4,6-triphenylbenzenesulfinate | 1 | 97 |
| Example 6 | 2,2-bis[4-(3-methacryloyloxy-2-hydroxypropoxy)phenyl]propane | 40 | sodium 2,4,6-triisopropylbenzenesulfinate | 1 | 96 |
| | triethylene glycol dimethacrylate | 30 | | | |
| | 1,2-bis(3-methacryloyloxy-2-hydroxypropoxy)ethane | 30 | | | |
| Example 7 | 2,2-bis[4-(3-methacryloyloxy-2-hydroxypropoxy)phenyl]propane | 40 | calcium 2,6-diisopropylbenzenesulfinate | 1 | 98 |
| | triethylene glycol dimethacrylate | 30 | | | |
| | 1,2-bis(3-methacryloyloxy-2-hydroxypropoxy)ethane | 30 | | | |
| Comparative Example 1 | 2-hydoxyethyl methacrylate | 100 | sodium benzenesulfinate | 1 | 10 |
| Comparative Example 2 | 2-hydoxyethyl methacrylate | 100 | sodium p-toluenesulfinate | 1 | 8 |
| Comparative Example 3 | 2-hydoxyethyl methacrylate | 100 | sodium p-ethylbenzenesulfinate | 1 | 8 |
| Comparative Example 4 | 2-hydoxyethyl methacrylate | 100 | sodium p-isopropylbenzenesulfinate | 1 | 7 |
| Comparative Example 5 | 2-hydoxyethyl methacrylate | 100 | calcium p-isopropylbenzenesulfinate | 1 | 9 |
| Comparative Example 6 | 2-hydoxyethyl methacrylate | 100 | calcium o-isopropylbenzenesulfinate | 1 | 38 |
| Comparative Example 7 | 2-hydoxyethyl methacrylate | 100 | sodium 2,4,6-trimethylbenzenesulfinate | 1 | 55 |
| Comparative Example 8 | 2,2-bis[4-(3-methacryloyloxy-2-hydroxypropoxy)phenyl]propane | 40 | sodium benzenesulfinate | 1 | 13 |
| | triethylene glycol dimethacrylate | 30 | | | |
| | 1,2-bis(3-methacryloyloxy-2-hydroxypropoxy)ethane | 30 | | | |

Example 8 and Comparative Example 9

The following compositions A and B were prepared.

| | Parts by weight |
|---|---|
| Composition A | |
| 2,2-Bis[4-(3-methacryloyloxy-2-hydroxypropoxy)phenyl]propane | 40 |
| Triethylene glycol dimethacrylate | 30 |
| 2-Hydroxyethyl methacrylate | 30 |
| Sodium 2,4,6-triisopropylbenzenesulfinate | 1 |
| N,N-Diethanol-p-toluidine | 2 |
| Quartz powder silane-treated | 300 |
| Composition B | |
| 2,2-Bis[(4-(3-methacryloyloxy-2-hydroxypropoxy)phenyl]propane | 40 |
| Triethylene glycol dimethacrylate | 30 |
| 10-Methacryloyloxydecyl dihydrogenphosphate | 30 |
| Benzoyl peroxide | 2 |
| Quartz powder silane-treated | 300 |

The composition A just after preparation and that after having been stored at 25° C. for 1 year were each subjected to the following test 1. Further these were combined with composition B and subjected to the following tests 2, 3 and 4.

Test 1

To 0.5 g of composition A 5 ml of methanol was added, the mixture was stirred well and the quartz powder was removed from the mixture by filtration. The amount of sodium 2,4,6-triisopropylbenzenesulfinate in the methanol solution was determined by high-performance liquid chromatography. The ratio of the amount of sodium 2,4,6-triisopropylbenzenesulfinate after storage to that just after preparation was calculated. The results are shown in Table 2.

Test 2

Equal amounts of compositions A and B were kneaded together for 30 seconds, and the mixture was filled in a teflon container having an inside diameter of 5 mm and a depth of 7 mm, and tested for curing or hardening time. A thermocouple was inserted in the kneaded mixture and temperature change was recorded. Time required until the stoppage of temperature increase due to polymerization heat was taken as the curing time. The results are shown in Table 2.

Test 3

A test surface to be bonded was prepared by patching an adhesive tape with a hole having a diameter of 5 mm to the surface of a nickel-chrome alloy plate (Now Chrom (I), made by Towa Giken Co.) ground with 1000-grit silicon-carbide abrasive paper. Round rods of SUS304 and having a diameter of 7 mm and a length of 25 mm were sand blasted on their end surface with alumina abrasive powder of particle size of 50 μm. On the blasted end a paste obtained by kneading equal amounts of compositions A and B was heaped and the paste was pressed onto the test surface to bond the rod to the surface. After 1 hour the test piece thus prepared was immersed in water at 37° C. and kept therein for 24 hours, and then tested for tensile bond strength using a universal tensile testing machine (Instron) at a crosshead speed of 2 mm/min. An average of measurements on 10 test pieces was calculated. The results are shown in Table 2.

Test 4

A labial enamel surface of bovine tooth was ground with silicon-carbide abrasive paper to be flat, and the flat surface was etched with a 40% aqueous phosphoric acid solution for 1 minute. On the etched surface an adhesive tape with a hole having a diameter of 5 mm was patched to prepare a test surface to be bonded. Round rods of SUS304 and having a diameter of 7 mm and a length of 25 mm were sand blasted on their end surface with alumina abrasive powder of particle size of 50 μm. On the blasted end a paste obtained by kneading equal amounts of compositions A and B was heaped and the paste was pressed onto the test surface to bond the rod to the surface. After 1 hour the test piece thus prepared was immersed in water at 37° C. and kept therein for 24 hours, and then tested for tensile bond strength using Instron at a crosshead speed of 2 mm/min. An average of measurements on 10 test pieces was calculated. The results are shown in Table 2.

This Example 8 was repeated except for preparing the composition by using sodium benzenesulfinate instead of sodium 2,4,6-triisopropylbenzenesulfinate of composition A. This is Comparative Example 9 in Table 2.

required until the stoppage of temperature increase due to polymerization heat was taken as the curing time.

Example 10

The following compositions D and E were prepared, and, after being stored at room temperature for 1 year, tested for adhesiveness to human tooth dentine.

| | Parts by weight |
|---|---|
| Composition D | |
| 2,2-Bis[4-(3-methacryloyloxy-2-hydroxypropoxy)phenyl]propane | 20 |
| 2-Hydroxyethyl methacrylate | 80 |
| Sodium 2,4,6-triisopropylbenzenesulfinate | 3 |
| N,N-Dimethyl-p-toluidine | 2 |
| 2,6-Di-t-butyl-4-methylphenol | 0.03 |
| Composition E | |
| 2,2-Bis[4-(3-methacryloyloxy-2-hydroxypropoxy)phenyl]propane | 35 |
| Neopentyl glycol dimethacrylate | 30 |
| 10-Methacryloyloxydecyl dihydrogenphosphate | 35 |
| Benzoyl peroxide | 2 |

TABLE 2

| | Example 8 | | Comparative Example 9 | |
|---|---|---|---|---|
| | Just after preparation | After storage at 25° C. for 1 year | Just after preparation | After storage at 25° C. for 1 year |
| Test 1 (Retention of suflinic acid salt) (%) | 100 | 89 | 100 | 0 |
| Test 2 (Curing time) | 8 min and 30 sec | 8 min and 55 sec | 8 min and 35 sec | not hardened |
| Test 3 (Bond strength to nickel-chrome alloy) (kg/cm$^2$) | 419 | 408 | 420 | not tested because this did not harden. |
| Test 4 (Bond strength to bovine tooth enamel) (kg/cm$^2$) | 160 | 156 | 159 | not tested because this did not harden. |

Example 9

The following composition C was prepared.

| Composition C | Parts by weight |
|---|---|
| 2,2-Bis[4-(3-methacryloyloxy-2-hydroxypropoxy)phenyl]propane | 40 |
| 1,6-Bismethacrylamidehexane | 30 |
| 2-Hydroxyethyl methacrylate | 30 |
| Sodium 2,4,6-triisopropylbenzenesulfinate | 1 |
| Camphorquinone | 1 |

A glass cylindrical sample tube having an inside diameter of 10 mm and a wall thickness of 0.8 mm was charged with 0.25 ml of the composition. The tube with its contents was irradiated from below through a visible light irradiator (Quick light, made by Kuraray Co., Ltd.), then the contents hardened in 32 seconds. A part of the above composition was stored at room temperature for 1 year, and then subjected to the same irradiation test, to harden in 35 seconds. In determining the curing time, a thermocouple was inserted in the composition and temperature change was recorded. Time -continued

| | Parts by weight |
|---|---|
| 2,6-Di-t-butyl-4-methylphenol | 0.03 |

Human molar tooth was ground with a silicon-carbide abrasive paper to expose the dentine, and then acid-etched with a 40% aqueous phosphoric acid solution for 1 minute. An adhesive tape with a hole having a diameter of 5 mm was patched on this etched surface to prepare a test surface to be bonded. Separately, pieces of round rod of SUS304 and having a diameter of 7 mm and a length of 25 mm were sand blasted on their end surface with alumina abrasive powder of particle size of 50 μm. A paste obtained by kneading equal amounts of compositions D and E was applied both on this blasted end surface and on the human tooth test surface prepared above. Kneaded paste of a commercially available dental composite resin (CLEARFIL FII, made by Kuraray Co.) was heaped on the end surface of the rod and the paste was pressed onto the human tooth test surface to bond the rod to the surface. After 1 hour the test piece thus prepared was immersed in water at 37° C. and kept therein for 24 hours, and then tested for tensile bond strength using Instron at a crosshead speed of 2 mm/min. An average of measurements on 8 test pieces was calculated to give 130 kg/cm².

Example 11

The compositions D and E stored at room temperature for 1 year as used in Example 10 were tested for metal-to-metal adhesiveness as follows.

Two pieces of round rod of SUS304 and having a diameter of 7 mm and a length of 25 mm were sand blasted on their end surface with alumina grinding powder of particle size of 50 μm. Composition D was applied to the blasted end surface of one rod, while composition E to that of the other rod. The two surfaces were pressed with each other to bond, to prepare a test piece. The test piece was kept at 25° C. for 24 hours, and then tested for tensile bond strength with Instron at a crosshead speed of 2 mm/min. An average of measurements on 10 test pieces was 382 kg/cm².

Having described the present invention, it will be apparent to the artisan that numerous modifications and variations of the present invention are possible in light of the above teachings. It is therefore to be understood that within the scope of the appended claims, the invention may be practiced otherwise than as specifically described herein, and that numerous modifications and variations may be made to the above disclosed embodiments without departing from the spirit and scope of the present invention.

What is claimed is:

1. A polymerizable composition, comprising:
   (a) a monomer;
   (b) a sulfinate having the formula (I):

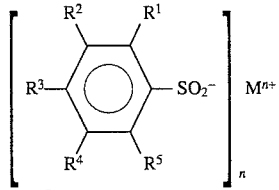

(I)

wherein $R^1$ and $R^5$ each represents a substituent having 2 to 6 carbon atoms, $R^2$, $R^3$ and $R^4$ each represents an atom or substituent inert to said monomer (a), $M^{n+}$ represents an n-valent cation, and n represents an integer of 1 to 2, and wherein said monomer has a carbon-carbon double bond directly linked to an electron attracting group.

2. The polymerizable composition according to claim 1, wherein said sulfinate is represented by the formula:

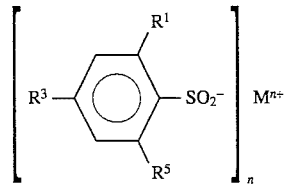

wherein $R^1$ and $R^5$ each represents a substituent having 2 to 6 carbon atoms, $R^3$ represents a substituent having 1 to 6 carbon atoms, a hydrogen atom or a halogen, $M^{n+}$ represents an alkali metal ion, an alkaline earth metal ion, a transition metal ion or an ammonium ion, and n represents an integer of 1 to 2.

3. The polymerizable composition according to claim 2, wherein said sulfinate of the formula (I) is used in an amount of 0.03 to 5% by weight.

4. The polymerizable composition according to claim 1, wherein said sulfinate is represented by the formula:

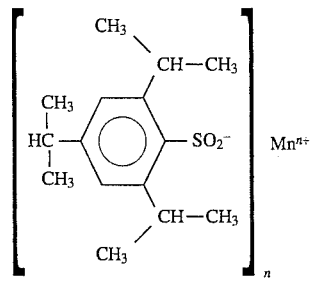

wherein $M^{n+}$ represents $Li^+$, $Na^+$, $K^+$, $Mg^{2+}$ or $Ca^{2+}$.

5. The polymerizable composition according to claim 1, wherein said monomer is an acrylate, a methacrylate, an α-haloacrylate, an acrylamide, a methacrylamide, an acrylamide derivative or a methacrylamide derivative.

6. A multiple-package system for preparing a polymerizable composition according to claim 1, comprising:
   (a) said monomer;
   (b) said sulfinate represented by the formula (I), and
   (c) an oxidizer; said (b) and (c) being stored in separate packages and mixed with each other to effect polymerization.

7. The multiple-package system according to claim 6, wherein said oxidizer is an organic peroxide.

8. The multiple-package system according to claim 6, wherein said oxidizer is an aromatic diacyl peroxide.

9. The polymerizable composition according to claim 8, wherein said diacyl peroxide is selected from the group consisting of benzoyl peroxide, m-toluoyl peroxide, 2,4-dichlorobenzoyl peroxide, octanoyl peroxide, lauroyl peroxide and succinoyl peroxide.

10. The multiple-package system according to claim 6, wherein said oxidizer is used in an amount of 0.01 to 500 parts by weight based on 1 part by weight of said sulfinate.

11. The polymerizable composition according to claim 11, comprising:
   (a) said monomer;
   (b) said sulfinate represented by the formula (I), and
   (c) a photoinitiator.

12. The polymerizable composition according to claim 11, wherein said photoinitiator is a photosensitive dye or an α-diketone.

13. A multiple-package system for preparing a polymerizable composition according to claim 1, comprising:
   (a) said monomer;
   (b) said sulfinate represented by the formula (I);
   (c) an oxidizer; and
   (d) an amine;
said oxidizer being stored in a separate package from (b) and (d).

14. The multiple-package system according to claim 13, wherein said amine is an aromatic secondary or tertiary amine.

15. The polymerizable composition according to claim 14, wherein said secondary or tertiary amine is selected from the group consisting of N,N-dimethylaniline, N,N-dimethyl-p-toluidene, ethyl m-N,N-dimethylaminobenzoate, ethyl p-N,N-dimethylaminobenzoate, N,N-diethanolaniline, N,N-diethanol-p-toluidine, N,N-diethanol-m-chloroaniline, N,N-bis(3-hydroxypropyl)aniline, N,N-bis(3-hydroxypropyl)-p-toluidine, N,N-bis(2,3-dihydroxypropyl)aniline, m-N,N- bis(2,3-dihydroxypropyl)aminobenzoate, N-methylaniline and N-methyl-p-toluidine.

16. The multiple-package system according to claim 13, wherein said amine is used in an amount of 0.01 to 500 parts by weight based on 1 part by weight of the compound of the formula (I).

17. The polymerizable composition according to claim 1, wherein said sulfinate of the formula (I) is used in an amount of 0.01 to 10% by weight based on the weight of the composition.

18. The polymerizable composition according to claim 1, wherein $R^1$ and $R^5$ are independently each ethyl, 2-chloroethyl, 2-bromo-2-chloroethyl, propyl, isopropyl, perfluoropropyl, allyl, butyl, isobutyl, sec-butyl, tert-butyl, pentyl, isopentyl, neopentyl, tert-pentyl, cyclohexyl, phenyl or 4-bromophenyl.

19. The polymerizable composition according to claim 1, wherein $R^2$, $R^3$ and $R^4$ are independently each hydrogen, fluoro, chloro, bromo, iodo, methyl, ethyl, 2-chloroethyl, 2-bromo-2-chloroethyl, propyl, isopropyl, perfluoropropyl, allyl, butyl, isobutyl, sec-butyl, tert-butyl, pentyl, isopentyl, neopentyl, tert-pentyl, cyclohexyl, phenyl or 4-bromophenyl.

20. The polymerizable composition according to claim 1, wherein said electron attracting group is —F, —Cl, —Br, —I, —CN, —NO$_2$, —NO, —CO, —CS, —COO—, —COS—, —CSO—, —CSS—, —CONH$_2$, —CONH— or —CON—.

\* \* \* \* \*

UNITED STATES PATENT AND TRADEMARK OFFICE
CERTIFICATE OF CORRECTION

PATENT NO. : 5,486,544

DATED : January 23, 1996

INVENTOR(S) : MITSUNOBU KAWASHIMA ET AL

It is certified that error appears in the above-identified patent and that said Letters Patent is hereby corrected as shown below:

Column 1, line 37, "wily" should read --will--.

Column 2, line 11, "formula" should read --formula (I)--.

Column 2, line 66, "$Ba^2$" should read --$Ba^{2+}$--.

Column 2, line 67, "$Co^{3+}$" should read --$Co^{3+}$--.

Column 3, line 5, "$CH_3\overset{H^+}{-}N-CH_3$" should read --$CH_3-\overset{H^+}{N}-CH_3$--.

Column 3, line 12, "$CH_3\overset{H}{-}N-CH_2CH_2OH$ and $HOCH_2CH_2\overset{H}{-}N-CH_2CH_2OH$" should read --$CH_3-\overset{H^+}{N}-CH_2CH_2OH$ and $HOCH_2CH_2-\overset{H^+}{N}-CH_2CH_2OH$--.

UNITED STATES PATENT AND TRADEMARK OFFICE
CERTIFICATE OF CORRECTION

PATENT NO. : 5,486,544

DATED : January 23, 1996

INVENTOR(S) : MITSUNOBU KAWASHIMA ET AL

It is certified that error appears in the above-identified patent and that said Letters Patent is hereby corrected as shown below:

Column 3, line 55, the formula:

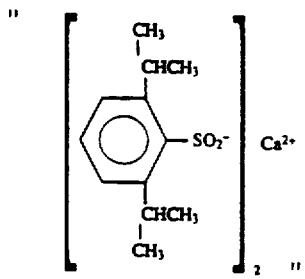  should read -- 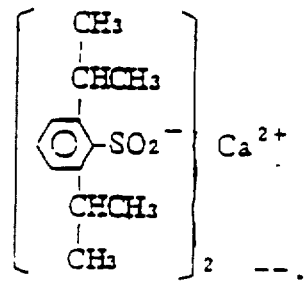 --.

Column 4, line 5, the formula:

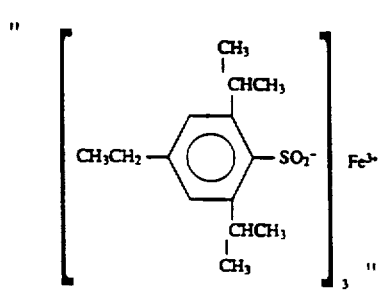  should read -- 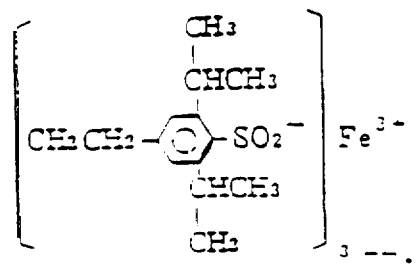 --.

UNITED STATES PATENT AND TRADEMARK OFFICE
CERTIFICATE OF CORRECTION

PATENT NO. : 5,486,544

DATED : January 23, 1996

INVENTOR(S) : MITSUNOBU KAWASHIMA ET AL

It is certified that error appears in the above-identified patent and that said Letters Patent is hereby corrected as shown below:

Column 4, line 12, the formula:

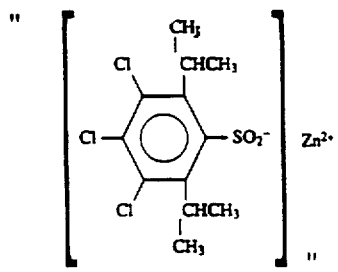   should read --   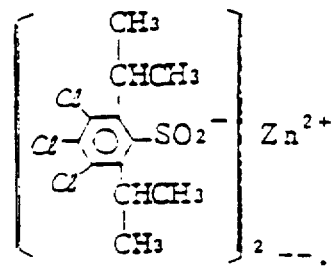

Column 4, line 24, the formula:

should read--

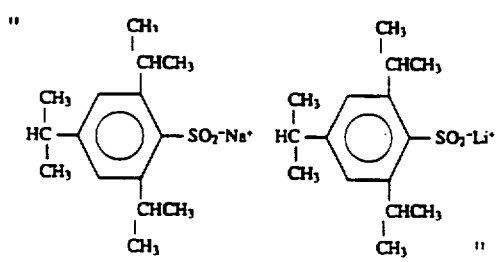   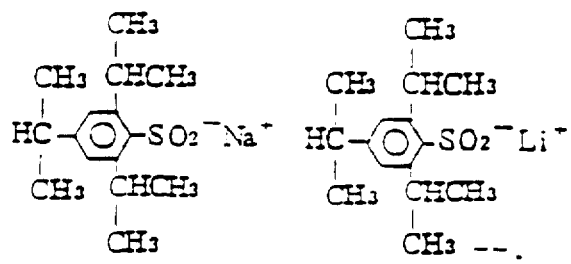  --.

UNITED STATES PATENT AND TRADEMARK OFFICE
CERTIFICATE OF CORRECTION

PATENT NO. : 5,486,544

DATED : January 23, 1996

INVENTOR(S) : MITSUNOBU KAWASHIMA ET AL

It is certified that error appears in the above-identified patent and that said Letters Patent is hereby corrected as shown below:

Column 4, line 34, the formula:

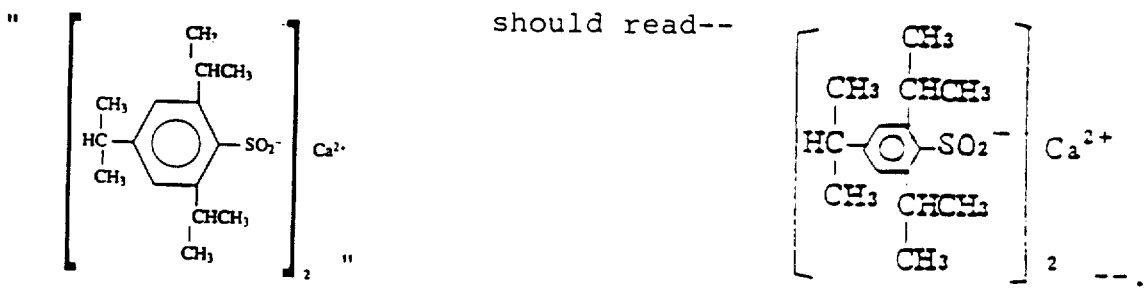

Column 4, line 44, the formula:

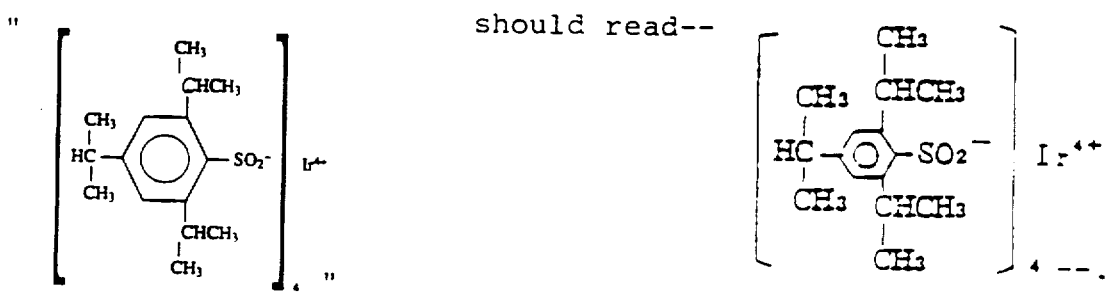

UNITED STATES PATENT AND TRADEMARK OFFICE
CERTIFICATE OF CORRECTION

PATENT NO. : 5,486,544

DATED : January 23, 1996

INVENTOR(S) : MITSUNOBU KAWASHIMA ET AL

It is certified that error appears in the above-identified patent and that said Letters Patent is hereby corrected as shown below:

Column 4, line 55, the formula:

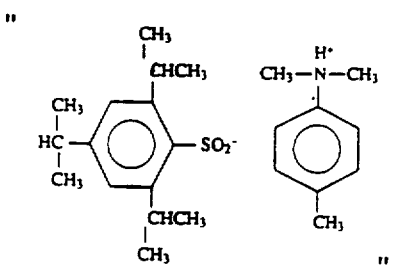      should read --      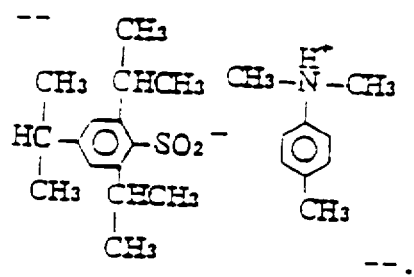    --.

Column 5, line 5, the formula:

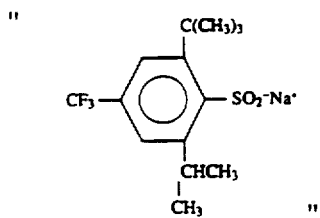      should read --      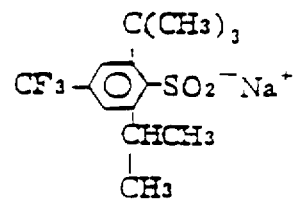    --.

UNITED STATES PATENT AND TRADEMARK OFFICE
CERTIFICATE OF CORRECTION

PATENT NO. : 5,486,544
DATED : January 23, 1996
INVENTOR(S) : MITSUNOBU KAWASHIMA ET AL It is certified that error appears in the above-identified patent and that said Letters Patent is hereby corrected as shown below:

Column 6, line 14, "O" should read --o--;

line 52, "N,N-dimethyl(math)acrylamide" should read --N,N-dimethyl(meth)acrylamide--.

Column 8, line 16, "denistry" should read --dentistry--;

line 34, "2hydroxypropoxy-" should read --2-hydroxypropoxy- --;

line 47, "pisopropylbenzenesulfinate" should read --p-isopropylbenzenesulfinate--.

Column 13, line 65, "claim 2" should read --claim 1--.

Column 14, line 40, "claim 11" should read --claim 1--;

line 67, "m-N,N-" should read --ethyl m-N,N- --.

Signed and Sealed this

Seventeenth Day of September, 1996

Attest:

BRUCE LEHMAN

Attesting Officer     Commissioner of Patents and Trademarks